United States Patent
Takizawa et al.

(10) Patent No.: US 6,548,786 B2
(45) Date of Patent: Apr. 15, 2003

(54) CIRCUIT FOR DRIVING A HEATER AT A CONSTANT POWER

(75) Inventors: Takashi Takizawa, Kawasaki (JP); Hiroshi Nishida, Akita (JP)

(73) Assignee: Fujikura, Ltd., Tokyo (JP)

( * ) Notice: Subject to any disclaimer, the term of this patent is extended or adjusted under 35 U.S.C. 154(b) by 35 days.

(21) Appl. No.: 09/851,112

(22) Filed: May 9, 2001

(65) Prior Publication Data
US 2001/0050279 A1 Dec. 13, 2001

(30) Foreign Application Priority Data
May 15, 2000 (JP) ........................................ 2000-141784

(51) Int. Cl.[7] ............................................. H05B 1/02
(52) U.S. Cl. ........................ 219/501; 219/508; 219/497
(58) Field of Search ................................ 219/216, 497, 219/505, 504, 499, 508; 323/235, 236

(56) References Cited

U.S. PATENT DOCUMENTS

| | | | | |
|---|---|---|---|---|
| 3,961,236 A | * | 6/1976 | Rodek et al. | ................. 323/18 |
| 4,542,281 A | * | 9/1985 | Thompson | ................... 219/216 |
| 4,660,057 A | * | 4/1987 | Watanabe et al. | ....... 346/140 R |
| 5,256,859 A | * | 10/1993 | Nanos et al. | ................ 219/492 |

* cited by examiner

*Primary Examiner*—Mark Paschall
(74) *Attorney, Agent, or Firm*—Sughrue Mion, PLLC

(57) ABSTRACT

A current-limiting resistor is connected between a power-supply line and a heater provided near the oxygen-detecting element of limiting-current type oxygen sensor. A power MOSFET is connected between the heater and a ground line. The resistor and the heater have such resistances that a current I2 flowing through the resistor and the heater when the heater has a resistance R2 is about $I1\sqrt{(R1/R2)}$, where I1 is a current flowing through the resistor and the heater when the heater has a resistance R1.

2 Claims, 2 Drawing Sheets

CIRCUIT FOR DRIVING A HEATER AT A CONSTANT POWER

CROSS-REFERENCE TO RELATED APPLICATIONS

This application is based upon and claims the benefit of priority from the prior Japanese Patent Application No. 2000-141784, filed May 15, 2000, the entire contents of which are incorporated herein by reference.

BACKGROUND OF THE INVENTION

1. Field of the Invention

The present invention relates to a circuit for driving a heater at a constant power, which is incorporated in, for example, a limiting-current type oxygen sensor.

2. Description of the Related Art

FIG. 4 shows a limiting-current type oxygen sensor 1. The oxygen sensor 1 comprises an ion conductor 2, two electrodes 3a and 3b, and a heater 4. The ion conductor 2 is made of, for example, stabilized zirconia. The electrodes 3a and 3b are made of porous material and provided on the upper and lower surfaces of the ion conductor 2, respectively. Gas containing oxygen ions is supplied to the electrode 3a, diffused and flowing at a regulated speed. As the oxygen ions move in the ion conductor 2, a current is generated. The current depends on the voltage applied across the ion conductor 2 and the temperature of the ion conductor 2.

Therefore, in the limiting-current type oxygen sensor 1, the heater 4 is arranged above an oxygen-detecting element (not shown). The heater 4 heats the oxygen-detecting element to a monitoring temperature of about 400° C. while the element is performing its function. The heater 4 is a pattern of platinum paste, which has been printed and sintered.

To keep heating the oxygen-detecting element at 400° C., the heater 4 needs to be driven at a constant power of, for example, about 1.5W. Formed by printing technology, heaters of this type 4 differ in thickness, width and the like. Inevitably, they have greatly different resistances. Consequently, the voltage applied to supply a constant electric power to one heater differs from the voltage applied to supply the same electric power to another heater.

Hitherto, a drive circuit of the structure shown in FIG. 3 has been used to drive a heater 4 of the type illustrated in FIG. 4. The drive circuit comprises a transistor 31, a diode 32, a resistors 33, 37 and 38, a trimmer potentiometer 34, a resistor 35, and an operational amplifier 36. The transistor 31 drives the heater 4, which is secured to the detecting element 2 of a limiting-current type oxygen sensor 1. The emitter of the transistor 31 is connected to the diode 32, which in turn is connected to a power supply. A voltage is applied to the heater 4 via the collector of the transistor 31. The collector of the transistor 31 is connected to the ground by the resistor 33, trimmer potentiometer 34 and resistor 35. The dial 34 adjusts the voltage, which is applied to one input terminal of the operational amplifier 36. The base of the transistor 31, which is biased by the resistor 37, receives the output of the operational amplifier 36 through the resistor 38. It is therefore necessary for the user to turn the dial of the trimmer potentiometer 34 so that an appropriate voltage may be applied to the heater 4.

For the manufacturer of the sensor 1 it is necessary to determine the voltage that should be applied to the heater 4 so that heater 4 may be driven at a predetermined power (e.g., 1.5W) and to record the data representing the voltage in a recording medium such as a data sheet and to secure the medium to or in the sensor 1. For the user of the sensor 1 it is necessary to turn the dial of the trimmer potentiometer 34 very carefully so that the voltage represented by the data recorded in the medium may be applied to the heater 4. Further, once the dial 34 has been turned so, the user needs to lock the rotor of the dial 34 by means of, for exampling, paint locking.

BRIEF SUMMARY OF THE INVENTION

The present invention has been made in view of the foregoing. An object of the invention is to provide a circuit that is designed to drive the heater at a constant power in a sensor and in which the voltage to apply to the heater need not be adjusted at all, rendering it unnecessary for the manufacturer or user of the sensor to take measures to adjust that voltage.

According to one aspect of the invention there is provided a circuit for driving a heater at a constant power. The circuit comprises: a current-limiting resistor to be connected in series to the heater provided in a limiting-current type oxygen sensor; and a drive element for driving, at a constant voltage, a series circuit constituted by the current-limiting resistor and the heater.

The power consumed in the heater can remain constant even if the heater has a resistance different from the design value. It is therefore unnecessary to secure a recording medium, such as a data sheet, to the medium to or in the limiting-current type oxygen sensor. Nor is it necessary to adjust the voltage applied to the heater. Thus, there will not arise a mismatching between the sensor and the data representing the voltage that should be applied to the heater so that heater 4 may be driven at a predetermined power. In addition, the user of the sensor need not turn any dial to apply an appropriate voltage to the heater. The circuit according to the invention can supply a constant power to the heater for a long period of time.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Embodiments of the present invention will be described, with reference to the accompanying drawings.

Figure 1:
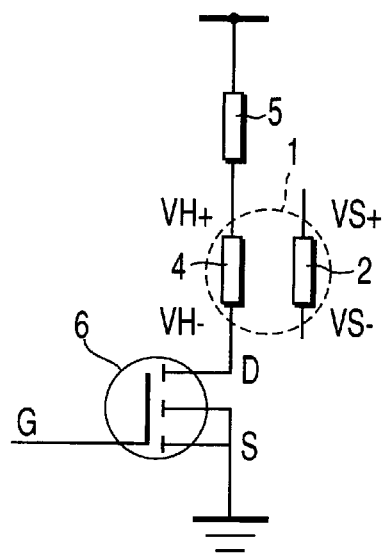
FIG. 1 is a diagram of a circuit according to the first embodiment of the invention, which is designed to drive a heater at a constant power.

FIG. 1 shows the first embodiment of the invention, or a circuit for driving a heater at a constant power. FIG. 1 shows a limiting-current type oxygen sensor 1, too, which comprises an oxygen-detecting element 2 and a heater 4. The circuit comprises a power-supply line, a ground line, a current-limiting resistor 5, and a power MOSFET 6. The resistor 5 is connected between the heater 4 and the power-supply line. The MOSFET 6 is connected between the heater 4 and the ground line. The circuit starts driving the heater 4 when an ON-signal is supplied to the gate of the MOSFET 6.

Assume that the power-supply voltage is 5V and about 0.1V should be applied to the MOSFET 6 to turn on the MOSFET 6. Then, about 4.9V is applied to the heater 4 and the resistor 5. If the heater 4 has a resistance of 3 Ω, the resistor 5 needs to have a resistance of about 3.9 Ω to supply power of, for example, 1.5W to the heater 4.

To render the power consumed in the heater 4 constant, the following equation should be satisfied:

$$R1 \cdot I1^2 = R2 \cdot I2^2$$

where R1 is the resistance of the heater 4, I1 is the current flowing through the heater 4 if the heater 4 has resistance R1 and I2 is the current flowing through the heater 4 if the heater 4 has resistance R2.

The equation is transformed into the following:

$$I2 = I1\sqrt{(R1/R2)}$$

If this equation is satisfied, the current flowing through the heater 4 will remain constant even if the resistance of the heater 4 changes.

Table 2 presented below shows the various powers the circuit that is the first embodiment of the invention supplies to heaters that have different resistances.

TABLE 1

Power-supply: DC 5V

| Current-limiting resistance (Ω) | Resistance of heater (Ω) | Current (A) | Power to heater (W) | Total power (W) |
|---|---|---|---|---|
| 3.9 | 2.0 | 0.83 | 1.38 | 4.07 |
| 3.9 | 2.5 | 0.77 | 1.47 | 3.75 |
| 3.9 | 3.0 | 0.71 | 1.51 | 3.48 |
| 3.9 | 3.5 | 0.66 | 1.53 | 3.24 |
| 3.9 | 4.0 | 0.62 | 1.54 | 3.04 |
| 3.9 | 4.5 | 0.58 | 1.53 | 2.86 |
| 3.9 | 5.0 | 0.55 | 1.52 | 2.70 |
| 3.9 | 5.5 | 0.52 | 1.49 | 2.57 |
| 3.9 | 6.0 | 0.49 | 1.47 | 2.43 |

Table 2 set forth below shows the various powers the circuit of the invention supplies to heaters that have different resistances, when the power-supply voltage is DC6V.

TABLE 2

Power-supply: DC 6V

| Current-limiting resistance (Ω) | Resistance of heater (Ω) | Current (A) | Power to heater (W) | Total power (W) |
|---|---|---|---|---|
| 5.6 | 2.0 | 0.78 | 1.21 | 4.58 |
| 5.6 | 2.5 | 0.73 | 1.33 | 4.30 |
| 5.6 | 3.0 | 0.69 | 1.41 | 4.05 |
| 5.6 | 3.5 | 0.65 | 1.47 | 3.83 |
| 5.6 | 4.0 | 0.61 | 1.51 | 3.63 |
| 5.6 | 4.5 | 0.58 | 1.54 | 3.45 |
| 5.6 | 5.0 | 0.56 | 1.55 | 3.28 |
| 5.6 | 5.5 | 0.53 | 1.55 | 3.14 |
| 5.6 | 6.0 | 0.51 | 1.55 | 3.00 |

As seen from Tables 1 and 2, the power consumed in the heater 4 falls within a range of 1.5W±0.1W even if the resistances of the heaters range from 3 Ω to 6 Ω. In other words, the power can be said to be constant.

Figure 2:
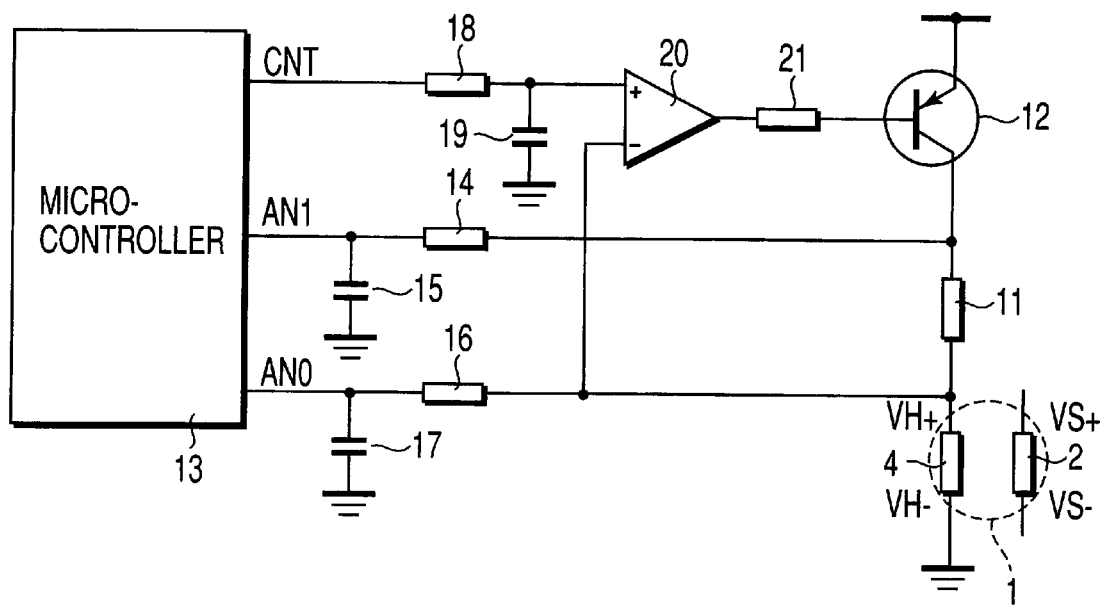
FIG. 2 is a diagram of a circuit according to the second embodiment of the invention, which is designed to drive a heater at a constant power.
Figure 3:
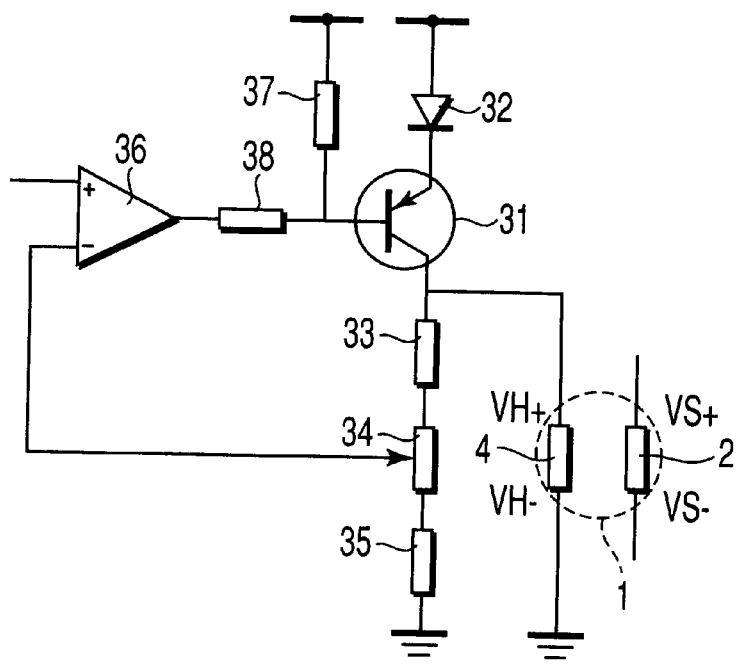
FIG. 3 is a diagram showing a conventional circuit for driving a heater at a constant power.
Figure 4:
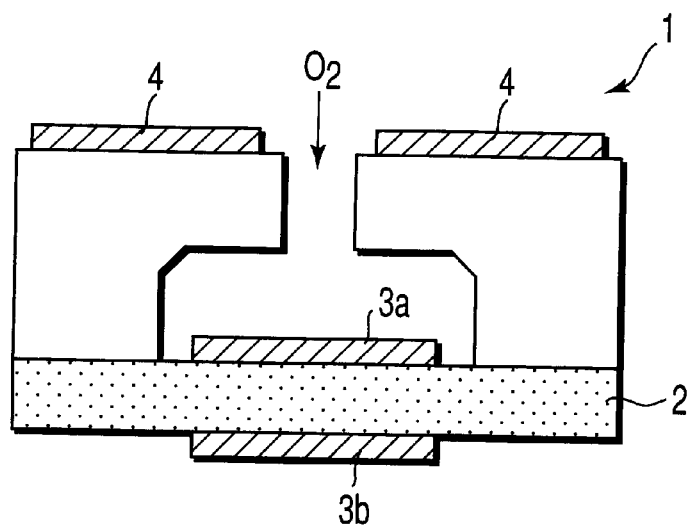
FIG. 4 is a sectional view of a limiting-current type oxygen sensor.

FIG. 2 illustrates the second embodiment of the invention, or a circuit for driving a heater at a constant power. FIG. 2 shows a limiting-current type oxygen sensor 1, too, which comprises an oxygen-detecting element 2 and a heater 4. The circuit comprises a power-supply line, a ground line, a resistor 11, and a transistor 12. The resistor 11 is connected in series to the heater 4 of the sensor 1, in order to detect a current. The transistor 12, which functions as a drive element, is connected between the resistor 11 and the power-supply line. The negative-potential terminal of the heater 4 is connected to the ground.

The circuit further comprises a micro-controller 13, an operational amplifier 20, a resistor 21, and three integrators. The voltage at the node of the resistor 11 and the collector of the transistor 12 is applied to the AN1 terminal of the micro-controller 13 via the first integrator that comprises a resistor 14 and a capacitor 15. The voltage at the node of the resistor 11 and the heater 4 is applied to the AN0 terminal of the micro-controller 13 via the second integrator that comprises a resistor 16 and a capacitor 17.

The micro-controller 13 incorporates an A/D converter (not shown). The voltages applied to the AN0 and AN1 terminals are converted to digital data items. The micro-controller 13 detects the current flowing in the resistor 11 from the voltage that is applied between the AN0 and AN1 terminals. The micro-controller 13 detects the voltage applied to the heater 4, from the voltage that is applied to the AN0 terminal. The micro-controller 13 generates a control signal CNT from the current and voltage that have been detected. The control signal CNT has a pulse width that is adjusted in accordance with the program stored in the micro-controller, so that the heater 4 may consume power of 1.5W.

The control signal CNT is input to the inverting input of the operational amplifier 20 through the third integrator that comprises a resistor 18 and a capacitor 18. The heater voltage is applied to the non-inverting input of the operational amplifier 20. The operational amplifier 20 controls the transistor 12 so that the voltages applied to the two inputs may become equal.

The resistance of the resistor 11 for detecting a current may be 1 Ω, for example. In this case, the current flowing in the heater 4 is the difference between the currents supplied to the AN1 and AN0 terminals of the micro-controller 13, i.e., AN1−AN0. It follows that the power the heater 4 consumes is (AN1−AN0)×AN0. The micro-controller 13 adjusts the pulse width of its output (i.e., control signal CNT) that is a rectangle-wave signal, in accordance with the program stored in it. Having the pulse width thus adjusted, the control signal CNT renders the power consumed in the heater 4 constant. The circuit of FIG. 2 makes it unnecessary to adjust the voltage applied to the heater 4.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A circuit for driving a heater at a constant power, comprising:

a current-limiting resistor to be connected in series to the heater provided in a limiting-current type oxygen sensor; and a drive element for driving, at a constant voltage, a series circuit constituted by the current-limiting resistor and the heater, wherein the current-limiting resistor and the heater have such resistances that a current I2 flowing through the current-limiting resistor and the heater when the heater has a resistance R2 is about $I1\sqrt{(R1/R2)}$, where I1 is a current flowing through the current-limiting resistor and the heater when the heater has a resistance R1.

2. A circuit for driving a heater at a constant power, comprising:

a current-detecting resistor to be connected in series to the heater provided in a limiting-current type oxygen sensor;

a drive element for driving, at a constant voltage, a series circuit constituted by the current-limiting resistor and the heater; and a controller for detecting a current flowing through the current-detecting resistor from a voltage applied between the ends of the current-detecting resistor and for controlling the drive element in accordance with the current detected and the voltage applied between the ends of the heater, thereby causing the power consumed in the heater to fall within a predetermined range, wherein the controller generates a rectangle-wave signal that has a pulse width adjusted so that the power consumed in the heater falls within the predetermined range.

* * * * *